United States Patent [19]
Neumann et al.

[11] Patent Number: 5,885,988
[45] Date of Patent: Mar. 23, 1999

[54] BENZO[G]QUINOLINE DERIVATIVES

[75] Inventors: Peter Neumann, Bern; Paul Pfaeffli, Oberwill; Max Peter Seiler, Riehen; Robert Swoboda, Koeniz, all of Switzerland

[73] Assignee: Novartis AG, Basel, Switzerland

[21] Appl. No.: 983,535

[22] PCT Filed: Jul. 5, 1996

[86] PCT No.: PCT/EP96/02969

§ 371 Date: Jan. 7, 1998

§ 102(e) Date: Jan. 7, 1998

[87] PCT Pub. No.: WO97/03054

PCT Pub. Date: Jan. 30, 1997

[30] Foreign Application Priority Data

Jul. 7, 1995 [GB] United Kingdom .................... 9513880
Feb. 26, 1996 [GB] United Kingdom .................... 9603988

[51] Int. Cl.[6] ........................ A61K 31/54; A61K 31/485; C07D 221/08; C07D 401/06
[52] U.S. Cl. ..................................... 514/224.5; 514/229.8; 514/250; 514/253; 544/32; 544/101; 544/344; 544/361
[58] Field of Search ............................... 544/32, 101, 344, 544/361; 514/224.5, 229.8, 250, 253

[56] References Cited

FOREIGN PATENT DOCUMENTS

| | | |
|---|---|---|
| 077 754 | 4/1983 | European Pat. Off. . |
| 641787 | 3/1995 | European Pat. Off. . |
| 2 160 200 | 12/1985 | United Kingdom . |
| 2 198 129 | 6/1988 | United Kingdom . |

OTHER PUBLICATIONS

R. Nordmann et al., Journal of Medicinal Chemistry vol. 28, No. 3, pp. 367–375, 1985.*
Derwent Abstract No. 90–187076, Sandoz, 1990.
Derwent Abstract No. 90–067066, Sandoz, 1990.
Derwent Abstract No. 95–225954, Sandoz, 1995.
Derwent Abstract No. 87–236766, Takeda Chemical, 1987.
Derwent Abstract No. 87–215340, Sandoz, 1987.

*Primary Examiner*—Emily Bernhardt
*Attorney, Agent, or Firm*—Joseph J. Borovian

[57] ABSTRACT

The invention provides compounds of formula I

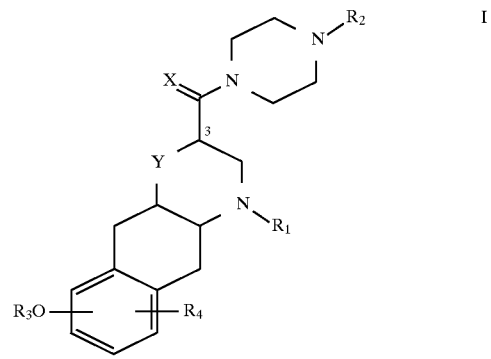

wherein X, Y, $R_1$, $R_2$, $R_3$ and $R_4$ are as defined in the description, and a process for preparing them. The compounds of formula I are useful as pharmaceuticals.

6 Claims, No Drawings

BENZO[G]QUINOLINE DERIVATIVES

The present invention relates to novel benzo[g]quinoline derivatives, their preparation, their use as pharmaceuticals and pharmaceutical compositions comprising them.

More particularly the present invention provides a compound of formula I

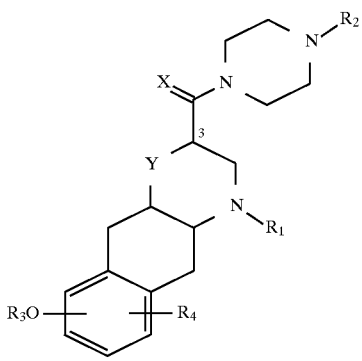

wherein

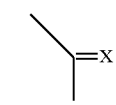

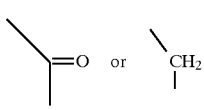

Y is —$CH_2$—, —O—, —NH— or —S—,
$R_1$ is H or ($C_{1-4}$)alkyl,
$R_2$ is H, benzyl, pyrimidyl, bis(4-fluorophenyl)methyl or a group of formula

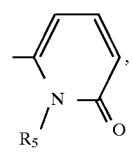  (a)

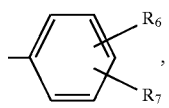  (b)

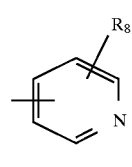  (c)

or

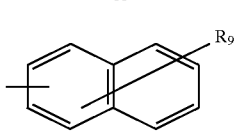  (d)

wherein $R_5$ is H or ($C_{1-4}$)alkyl and $R_6$, $R_7$, $R_8$ and $R_9$ independently are H, OH, $NO_2$, $CF_3$, ($C_{1-4}$)alkyl, acetyl, $CONR_{10}R_{11}$, $COOR_{12}$ [$R_{10}$, $R_{11}$ and $R_{12}$ independently being H or ($C_{1-4}$)alkyl], CN or ($C_{1-4}$)alkylsulfonyl,
$R_3$ is H, ($C_{1-4}$)alkyl, ($C_{1-4}$)alkylsulfonyl, trifluoromethylsulfonyl or a group of formula

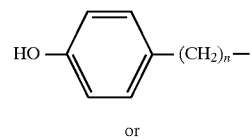

wherein n is 1 to 5 and m is 1 to 3, and
$R_4$ is hydrogen or halogen,
in free base or acid addition salt form.

The invention includes the enantiomers as well as their mixtures, e.g. the epimeric or racemic mixtures which may be present on account of the asymmetrical carbon atoms in positions 3, 4a and 10a. The configuration [3R,4aR,10aR] is preferred.

Halogen is fluorine, chlorine, bromine or iodine, preferably chlorine or bromine.

The above-defined alkyl groups preferably represent methyl.

In one group of compounds of formula I, X, Y and $R_1$ are as defined above, $R_2$ is H, benzyl, pyrimidyl, bis(4-fluorophenyl)methyl, naphthyl or a group of formula (a) as defined above or (b') or (c')

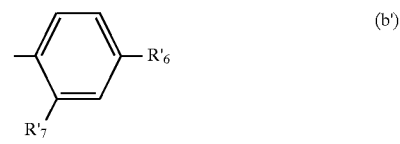  (b')

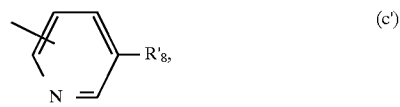  (c')

wherein $R'_6$ and $R'_7$ independently are H, OH, $NO_2$, $CF_3$, acetyl, $COOR_{12}$ ($R_{12}$ being as defined above) or CN and $R'_8$ is H, $NO_2$ or CN; $OR_3$ is in position 6 and $R_3$ is H, ($C_{1-4}$)alkyl, methylsulfonyl, trifluoromethylsulfonyl or a group of formula

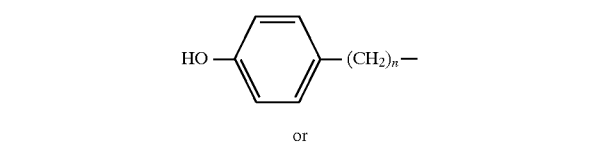

wherein n and m are as defined above, and $R_4$ is hydrogen, the configuration in positions 4a and 10a being R.

In another group of compounds of formula I,

is

Y is —CH$_2$— and R$_1$, R$_2$, R$_3$ and R$_4$ are as defined above.

In a further aspect, the invention provides a process for the production of the compounds of formula I and their acid addition salts, whereby a compound of formula II

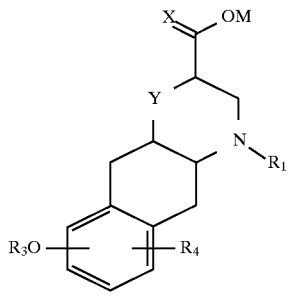

II wherein

Y, R$_1$, R$_3$ and R$_4$ are as defined above and M is H or an alkali metal, is reacted with a compound of formula III

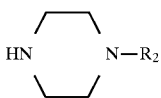

III wherein R$_2$ is as defined above, and the compounds of formula I thus obtained are recovered in free base or acid addition salt form.

The reaction can be effected according to known amide formation methods, for example as described in Example 1. In formula II, M as an alkali metal is for example sodium.

Working up the reaction mixtures obtained according to the above process and purification of the compounds thus obtained may be carried out in accordance to known procedures.

Acid addition salts may be produced from the free bases in known manner, and vice versa. Suitable acid addition salts for use in accordance with the present invention include for example the hydrochloride.

The starting compounds of formula II may be produced from the corresponding compounds of formula IV

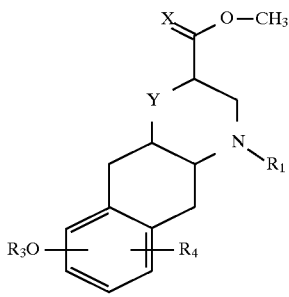

IV wherein

Y, R$_1$, R$_3$ and R$_4$ are as defined above, for example as described in Example 1.

The compounds of formulae III and IV are known or may be produced in analogous manner to known procedures. See for example European Patent No. 77754.

Compounds of formula I and their pharmaceutically acceptable acid addition salts, hereinafter referred to as agents of the invention, exhibit valuable pharmacological properties when tested in vitro using SRIF receptor expressing cell cultures and in animals, and are therefore useful as pharmaceuticals.

In particular the agents of the invention bind to somatostatin receptors. More particularly, they are selective antagonists at Somatostatin sst$_1$ receptors, previously called SSTR-1 receptors (see Hoyer et al., TiPS, 1995, 16; 86–88), as determined in radioligand binding and second messenger studies [see for example K. Kaupmann et al., FEBS LETTERS 1993, 331:53–59] where they exhibit selective affinity for sst$_1$ receptors with pIC$_{50}$ values between about 7.5 and 9.5.

The agents of the invention are therefore useful for treatment in anxiety, depression, schizophrenia, neurodegenerative diseases such as dementia, for the treatment of tumors and for vascular disorders and immunological diseases, as confirmed in a range of standard tests as indicated below:

At doses of about 0.3 to 3 mg/kg p.o., the agents of the invention increase exploratory behavior of mice in the open half of the half enclosed platform, a model which is predictable for anxiolytic activity (Psychopharmacology, 1986, 89:31–37).

In the same half enclosed platform model, the agents of the invention at the above indicated doses also increase vigilance of the mice. The compounds are therefore indicated for the treatment of depression, schizophrenia and dementia, in particular of senile dementia of the Alzheimer type (SDAT).

In the intruder mouse test [Triangle, 1982, 21:95–105; J. Clin. Psychiatry, 1994, 55:9 (suppl. B) 4–7], the agents of the invention increase social investigation and reduce defensive ambivalence in the treated intruder mouse at indicated doses of about 1 to about 10 mg/kg s.c., suggesting an antidepressant profile like carbamazepine and lithium, a neuroleptic profile like clozapine and an anxiolytic profile like diazepam.

Furthermore at said doses the compounds of the invention reduce aggressive behavior (attacks, chases, bites) in the Matched Pairs Situation test in mice [Dixon et al., J. Clin. Psychiatry 55: (9) [Suppl. B] 4–7 (1994)]. Since as mentioned above they additionally attenuate defensive behaviors in the intruder mouse test, the compounds of the invention exhibit an ethopharmacological profile which is very similar to that of carbamazepine, lithium chloride and clozapine. They are therefore indicated for the treatment of affective disorders including bipolar disorders e.g. manic-depressive psychoses, extreme psychotic states e.g. mania, schizophrenia, and excessive mood swings where behavioral stabilization is desired. In addition, the compounds are indicated in anxiety states, generalized anxiety as well as social and agoraphobia, as well as those behavioural states characterized by social withdrawal e.g. negative symptoms.

The agents of the invention are also effective in the treatment of various kinds of tumors, particularly of $sst_1$ receptor bearing tumors, as indicated in proliferation tests with various different cancer cell lines and in tumor growth experiments in nude mice with hormone dependent tumors [see for example: G. Weckbecker et al., Cancer Research 1994, 54:6334–6337]. Thus the compounds are indicated in the treatment of, for example, cancers of the breast, the prostate, the colon, the pancreas, the brain and the lung (small cell lung cancer).

For all the above mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 10 mg/kg animal body weight. In larger mammals, for example humans, an indicated daily dosage is in the range from about 5 to about 200 mg, preferably about 10 to about 100 mg of the compound conveniently administered in divided doses up to 4 times a day or in sustained release form.

The agents of the invention may be administered in free form or in pharmaceutically acceptable salt form. Such salts may be prepared in conventional manner and exhibit the same order of activity as the free compounds.

Compounds having selective $sst_1$ antagonist activity, i.e. showing selective $sst_1$ receptor affinity in the above-mentioned binding test with $pIC_{50}$ values >7.0, have never previously been described in the art. Such compounds accordingly represent an entirely novel compound group.

Accordingly in a further aspect the present invention provides selective $sst_1$ receptor antagonists for use as pharmaceuticals, more specifically for treatment in the above-mentioned conditions, e.g. depression, anxiety and bipolar disorders.

The present invention furthermore provides a pharmaceutical composition comprising a selective $sst_1$ receptor antagonist, e.g. an agent of the invention in association with at least one pharmaceutically acceptable diluent or carrier. Such compositions may be formulated in conventional manner. Unit dosage forms contain, for example, from about 0.25 to about 50 mg of an agent according to the invention.

Selective $sst_1$ receptor antagonists, e.g. agents of the invention may be administered by any conventional route, for example parenterally e.g. in form of injectable solutions or suspensions, or enterally, preferably orally, e.g. in the form of tablets or capsules.

For all the above indications the preferred compound is [3R,4aR,10aR]-1,2,3,4,4a,5,10, 10a-octahydro-6-methoxy-1-methyl-benzo[g]quinoline-3-carboxylic acid 4-(4-nitro-phenyl)-piperazine amide, which is the compound of example 1. Said compound has high affinity for rat $sst_1$ receptors ($pIC_{50}$=9.1) and recombinant human $sst_1$ receptors ($pIC_{50}$=7.7), without significant activity for a wide range of neurotransmitter receptors. At 1–10 mg/kg s.c., the compound clearly lowers aggressive behavior in the above-mentioned Matched Pairs Situation test and reverses social withdrawal in the above-mentioned intruder mouse test. These effects are also observed with the standard anti-manic drugs lithium and carbamazepine at 3–30 mg/kg s.c., suggesting similar therapeutic effects in man. However, lithium and carbamazepine were found to be less potent and are known to have considerable drawbacks such as narrow therapeutic window and slow onset of action.

The preferred indications are depression, anxiety and affective disorders, including bipolar disorders, e.g. mania.

In accordance with the foregoing, the present invention also provides the use of a selective $sst_1$ receptor antagonist, e.g. an agent of the invention, as a pharmaceutical, e.g. for the treatment of depression, anxiety and bipolar disorders.

Moreover the present invention provides the use of a selective $sst_1$ receptor antagonist, e.g. an agent of the invention, for the manufacture of a medicament for the treatment of any condition mentioned above, e.g. depression, anxiety and affective disorders.

In still a further aspect the present invention provides a method for the treatment of any condition mentioned above, e.g. depression, anxiety and bipolar disorders, in a subject in need of such treatment, which comprises administering to such subject a therapeutically effective amount of a selective $sst_1$ receptor antagonist, e.g. an agent of the invention.

The following examples illustrate the invention. The temperatures are given in degrees Celsius and are uncorrected.

EXAMPLE 1

[3R,4aR,10aR]-1,2,3,4,4a,5,10,10a-octahydro-6-methoxy-1-methyl-benzo[g]quinoline-3-carboxylic acid 4-(4-nitro-phenyl)-piperazine amide a) A mixture of 8.681 g (30 mmol) of [3R,4aR,10aR]-1-methyl-3β-methoxycarbonyl-6-methoxy-1,2,3,4,4aα, 5,10,10αβ-octahydro-benzo[g]quinoline, 36 ml of methanol, 36 ml of tetrahydrofuran and 36 ml of 1M aqueous sodium hydroxide solution is vigorously stirred during 16 hours at room temperature. After cooling to 0°, the reaction mixture is filtered and the product is washed with cold 2-propanol and dried at 600 in high vacuum. The so obtained sodium salt of [3R,4aR,10aR]-1-methyl-6-methoxy-1,2,3,4,4aα,5,10, 10αβ-octahydro-benzo[g]quinoline-3β-carboxylic acid has a m.p. >230° (decomposition); $[\alpha]D,20$=-138.3° (0.5% in dimethylformamide/water 50:50).

b) A suspension of 2.973 g (10 mmol) of the sodium salt obtained under a) in 24 ml of 38% propane-phosphonic anhydride in dimethylformamide (30 mmol) and 10 ml of absolute pyridine is stirred during 15 minutes at room temperature. After addition of 2.07 g (10 mmol) of 1-(4-nitrophenyl)-piperazine, stirring is continued for 16 hours at room temperature and 100 ml of toluene and 100 ml of 2M aqueous ammonia are added. The precipitated crystals are filtered off, washed with water and toluene, dried and recrystallized in toluene. The resulting title compound has a m.p. of 218°–221°. $[\alpha]D,20$=-128.7° (0.5% in dimethylformamide).

The compounds of formula I below are produced in analogous manner to example 1.

In the following [3R,4aR,10aR] compounds,

is

Y is $CH_2$, $R_1$ is methyl, $R_2$, $R_3$, $R_5$, $R_6$, $R_7$ and $R_8$ are as indicated ($OR_3$ is in position 6) and $R_4$ is H.

| Ex. | $R_2$ | $R_3$ | $R_5$ | $R_6$ | $R_7$ | $R_8$ | m.p. | $[\alpha]^{20}_D$ ** |
|---|---|---|---|---|---|---|---|---|
| 2 | H | Me | | | | | 120 | −136.2 |
| 3 | 2-(c) | " | | | | H | 190 | −121.4 |
| 4 | " | —SO$_2$CF$_3$ | | | | " | 174 | −106.3 |
| 5 | " | (4-OH—Ph)Pr | | | | " | 209 | −113.6 |
| 6 | 4-(c) | Me | | | | " | 185 | −137.0 |
| 7 | 2-pyrimidyl | " | | | | | 213 | −129.7 |
| 8 | benzyl | " | | | | | 130 | −119.5 |
| 9 | bis(4-F—Ph)-Me— | " | | | | | * | −97.9 |
| 10 | (b) | " | | 2-NO$_2$ | H | | * | −116.8 |
| 11 | " | " | | " | 4-CF$_3$ | | * | −99.5 |
| 12 | " | H | | 4-NO$_2$ | H | | 223 | −131.9 |
| 13 | " | —SO$_2$CF$_3$ | | " | " | | 106 | −113.6 |
| 14 | " | —SO$_2$Me | | " | " | | 188 | −123.4 |
| 15 | " | Me | | 2-CN | " | | * | −123.6 |
| 16 | " | " | | 4-CN | " | | 216 | −125.7 |
| 17 | 2-(c) | " | | | | 5-CN | 205 | −124.0 |
| 18 | 1-(d) $R_9$ = H | " | | | | | * | −121.3 |
| 19 | (b) | " | | 4-OH | H | | 287 | −116.7 |
| 20 | " | " | | 4-Ac | " | | 214 | −116.3 |
| 21 | " | " | | 4-CF$_3$ | " | | 119 | −110.4 |
| 22 | (a) | " | Me | | | | 192 | −118.3 |
| 23 | " | " | H | | | | 227 | −123.0 |
| 24 | 2-(c) | " | | | | 6-BnO | 147 | −100.0 |
| 25 | (b) | " | | 4-COOMe | H | | 251 | −124.0 |
| 26 | " | " | | 4-NH$_2$CO | " | | 260 | −104.9 |
| 27 | " | " | | 4-diEt-NCO | " | | 163 | −103.5 |
| 28 | " | " | | 2-CN | 4-NO$_2$ | | 191 | −121.3 |
| 29 | " | " | | 3-NO$_2$ | H | | 95 | −101.7 |
| 30 | " | " | | 2-MeSO$_2$ | 4-NO$_2$ | | 271 | −92.9 |
| 31 | 1(d) $R_9$ = 6-CN | " | | | | | 195 | −106 |
| 32 | 1(d) $R_9$ = 7-CN | " | | | | | 195 | −106 |
| 33 | 1(d) $R_9$ = 8-Cl | " | | | | | 245 | −101 |

In the following racemates,

is

Y is O, $R_1$ is methyl, $R_2$, $R_3$, $R_5$, $R_6$, $R_7$ and $R_8$ are as indicated (OR$_3$ is in position 6) and $R_4$ is H.

| Ex. | $R_2$ | $R_3$ | $R_5$ | $R_6$ | $R_7$ | $R_8$ | m.p. | Config. |
|---|---|---|---|---|---|---|---|---|
| 34 | 2-(c) | Me | | | H | | 179 | (1) |
| 35 | " | " | | | " | | 167 | (2) |
| 36 | (b) | " | | 4-NO$_2$ | H | | 176 | (1) |
| 37 | " | " | | " | " | | 222 | (2) |
| 38 | 2-(c) | " | | | 6-CF$_3$ | | 154 | (1) |
| 39 | " | " | | | " | | 142 | (2) |
| 40 | " | " | | | 3-CF$_3$ | | 138 | (1) |

In following [3aR,4aR,10aR] compound,

is

Y is CH$_2$, $R_1$ is methyl, $R_2$, $R_3$, $R_5$, $R_6$, $R_7$ and $R_8$ are as indicated (OR$_3$ is in position 6) and $R_4$ is 9-Br.

| Ex. | $R_2$ | $R_3$ | $R_5$ | $R_6$ | $R_7$ | $R_8$ | m.p. | $[\alpha]^{20}_D$ ** |
|---|---|---|---|---|---|---|---|---|
| 41 | (a) | Me | | | | Me | 216 | −98.6 |

In the following [3aR,4aR,10aR] compound,

is

Y is CH₂, R₁ is H, R₂, R₃, R₅, R₆, R₇ and R₈ are as indicated (OR₃ is in position 6) and R₄ is H.

| Ex. | R₂ | R₃ | R₅ | R₆ | R₇ | R₈ | m.p. | $[\alpha]^{20}_D$*** |
|---|---|---|---|---|---|---|---|---|
| 42 | (b) | Me | | 4-NO₂ | H | | 226 | −115.5 |

In the following racemate,

is

Y is S, R₁ is methyl, R₂, R₃, R₅, R₆, R₇ and R₈ are as indicated (OR₃ is in position 6) and R₄ is H.

| Ex. | R₂ | R₃ | R₅ | R₆ | R₇ | R₈ | m.p. | Config. |
|---|---|---|---|---|---|---|---|---|
| 43 | 2-(c) | Me | | | | H | 128 | (2) |

In the following racemate,

is

Y is CH₂, R₁, is methyl, R₂, R₃, R₅, R₆, R₇ and R₈ are as indicated (OR₃ is in position 7) and R₄ is H.

| Ex. | R₂ | R₃ | R₅ | R₆ | R₇ | R₈ | m.p. (decomp.) | Config. |
|---|---|---|---|---|---|---|---|---|
| 44 | (b) | Me | | 4-NO₂ | H | | 284 | (1) |

Me = methyl
Et = Ethyl
Pr = propyl
Ph = phenyl
Bn = Benzyl
Ac = acetyl
*amorphous
**0.5% in DMF
***0.25% in DMF (1) = [3RS, 4aRS, 10aRS] racemate
(2) = [3SR, 4aRS, 10aRS] racemate

EXAMPLE 45

[3S,4aS,10aS]-1,2,3,4,4a,5,10,10a-octahydro-6-methoxy-1-methyl-benzo[g]quinoline-3-carboxylic acid 4-(4-nitro-phenyl)-piperazine amide Optical isomer of the compound of example 1, produced in analogous manner to example 1. M.p. (HCl salt)=254°; $[\alpha]^{20}_D$ (free base)=+135.3° (0.5% in DMF).

We claim:
1. A compound of formula I

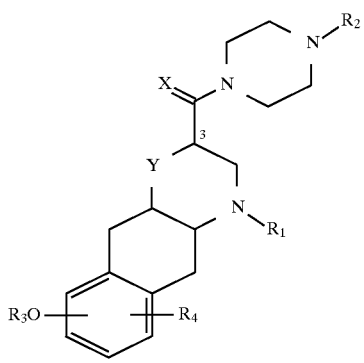

wherein

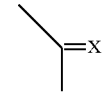

is

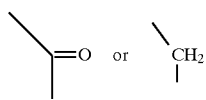

Y is —CH₂—, —O—, —NH— or —S—,
R₁ is H or (C₁₋₄)alkyl,
R₂ is H, benzyl, pyrimidyl, bis(4-fluorophenyl)methyl or a group of formula

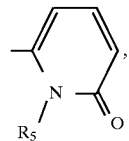

(a)

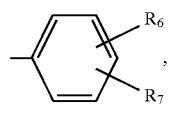

(b)

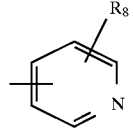

(c)

-continued

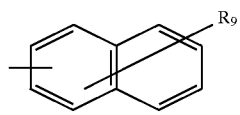

wherein $R_5$ is H or $(C_{1-4})$alkyl and $R_6$, $R_7$, $R_8$, and $R_9$ independently are H, OH, $NO_2$, $CF_3$, $(C_{1-4})$alkyl, acetyl, $CONR_{10}R_{11}$, $COOR_{12}$ [$R_{10}$ $R_{11}$ and $R_{12}$ independently being H or $(C_{1-4})$alkyl], CN or $(C_{1-4})$alkylsulfonyl, $R_3$ is H, $(C_{1-4})$alkyl, $(C_{1-4})$alkylsulfonyl, trifluoromethylsulfonyl or a group of formula

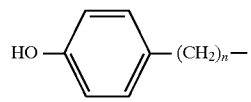

or

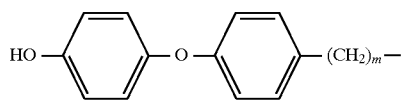

wherein n is 1 to 5 and m is 1 to 3, and $R_4$ is hydrogen or halogen in free base or acid addition salt form.

2. A compound according to claim 1, wherein

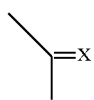

Y and $R_1$ are as defined in claim 1, $R_2$ is H, benzyl, pyrimidyl, bis(4-fluorophenyl)methyl, naphthyl or a group of formula (a) as defined in claim 1 or of formula (b') or (c')

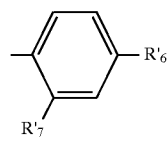

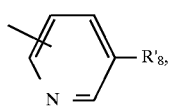

wherein $R'_6$ and $R'_7$ independently are H, OH, $NO_2$, $CF_3$, acetyl, $COOR_{12}$ ($R_{12}$ being as defined in claim 1) or CN and $R'_8$ is H, $NO_2$ or CN, $OR_3$ is in position 6 and $R_3$ is H, $(C_{1-4})$alkyl, methylsulfonyl, trifluoromethylsulfonyl or a group of formula

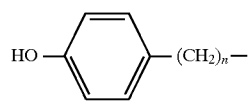

or

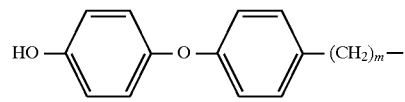

wherein n and m are as defined in claim 1 and $R_4$ is hydrogen, the configuration in positions 4a and 10a being R, in free base or acid addition salt form.

3. A compound of claim 1 which is [3R, 4aR, 10aR]-1, 2, 3, 4, 4a, 5, 10, 10a-octahydro-6-methoxy-1-methyl-benzo[g]quinoline-3-carboxylic acid 4-(4-nitro-phenyl)-piperazine amide, in free base or acid addition salt form.

4. A process for the preparation of a compound of formula I as defined in claim 1, or a salt thereof, which includes the step of reacting a compound of formula II

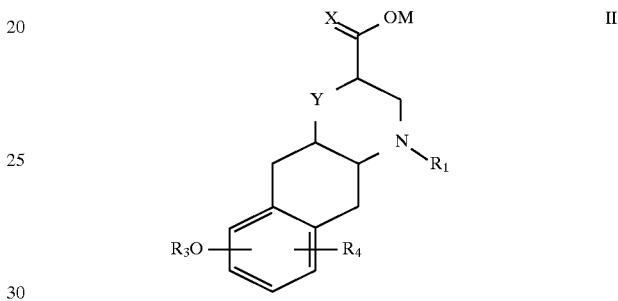

wherein

Y, $R_1$, $R_3$ and $R_4$ are as defined in claim 1 and M is H or an alkali metal, with a compound of formula III

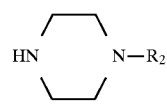

wherein $R_2$ is as defined in claim 1, and recovering the thus obtained compound of formula I in free base or acid addition salt form.

5. A pharmaceutical composition comprising a pharmaceutically acceptable carrier or diluent and a therapeutically effective amount of a compound of formula I according to claim 1, in free base or pharmaceutically acceptable acid addition salt form.

6. A method of treating depression, anxiety or bipolar disorders in a subject in need of such treatment comprising administering to said subject a therapeutically effective amount of a compound of formula I according to claim 1, in free base or pharmaceutically acceptable acid addition salt form.

* * * * *